United States Patent
Mizuno

(10) Patent No.: US 11,265,483 B2
(45) Date of Patent: Mar. 1, 2022

(54) ENDOSCOPIC IMAGE PROCESSING APPARATUS AND ENDOSCOPE SYSTEM

(71) Applicant: OLYMPUS CORPORATION, Tokyo (JP)

(72) Inventor: Kyosuke Mizuno, Hino (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 17/099,026

(22) Filed: Nov. 16, 2020

(65) Prior Publication Data
US 2021/0075974 A1    Mar. 11, 2021

Related U.S. Application Data

(63) Continuation of application No. PCT/JP2019/020418, filed on May 23, 2019.

(30) Foreign Application Priority Data

May 23, 2018   (JP) .............................. JP2018-098973

(51) Int. Cl.
*H04N 5/225*   (2006.01)
*H04N 5/243*   (2006.01)
(Continued)

(52) U.S. Cl.
CPC .......... *H04N 5/243* (2013.01); *H04N 5/2351* (2013.01); *A61B 1/00009* (2013.01); *H04N 2005/2255* (2013.01)

(58) Field of Classification Search
CPC ................ H04N 5/243; H04N 5/2351; H04N 2005/2255; H04N 5/23293; H04N 5/23245; A61B 1/00009; G02B 23/26; G02B 23/24

See application file for complete search history.

(56) References Cited

U.S. PATENT DOCUMENTS

| 2003/0063398 A1 | 4/2003 | Abe et al. |
| 2013/0235258 A1* | 9/2013 | Shida ................. A61B 1/00186 348/370 |
| 2014/0171737 A1* | 6/2014 | Kagaya ............... H04N 5/2327 600/109 |

FOREIGN PATENT DOCUMENTS

| EP | 2 620 092 A1 | 7/2013 |
| EP | 2 742 849 A2 | 6/2014 |

(Continued)

OTHER PUBLICATIONS

International Search Report dated Jul. 30, 2019 received in PCT/JP2019/020418.

*Primary Examiner* — Howard D Brown, Jr.
(74) *Attorney, Agent, or Firm* — Scully, Scott, Murphy & Presser, P.C.

(57) ABSTRACT

An endoscopic image processing apparatus includes a memory configured to store a threshold THn to determine a dark region in the near-point image inputted, a brightness correction circuit configured to perform brightness correction on the near-point image based on the threshold THn depending on timing of acquiring the near-point image and perform second brightness correction on the far-point image based on a threshold THf on the far-point image, and a light distribution state determination circuit configured to determine whether a light distribution state of a live image from an endoscope is a light distribution state of the near-point image. The brightness correction circuit, in the timing of acquiring the near-point image, performs the first brightness correction when the light distribution state determination circuit determines that the light distribution state of the live image is the light distribution state of the near-point image.

5 Claims, 5 Drawing Sheets

(51) Int. Cl.
*H04N 5/235* (2006.01)
*A61B 1/00* (2006.01)

(56) References Cited

FOREIGN PATENT DOCUMENTS

| | | | |
|---|---|---|---|
| JP | 61-46922 A | | 3/1986 |
| JP | 2003-102675 A | | 4/2003 |
| JP | 2006-081616 A | | 3/2006 |
| JP | 2006081616 A | * | 3/2006 |
| JP | 2012-090889 A | | 5/2012 |
| JP | 2014-117414 A | | 6/2014 |
| JP | 2016-129618 A | | 7/2016 |
| WO | 2012/056970 A1 | | 5/2012 |
| WO | 2013/180147 A1 | | 12/2013 |
| WO | 2017/022324 A1 | | 2/2017 |

* cited by examiner

ENDOSCOPIC IMAGE PROCESSING APPARATUS AND ENDOSCOPE SYSTEM

CROSS REFERENCE TO RELATED APPLICATION

This application is a continuation application of PCT/JP2019/020418 filed on May 23, 2019 and claims benefit of Japanese Application No. 2018-098973 filed in Japan on May 23, 2018, the entire contents of which are incorporated herein by this reference.

BACKGROUND OF THE INVENTION

1. Field of the Invention

The present invention relates to an endoscopic image processing apparatus and an endoscope system, and more particularly, to an endoscopic image processing apparatus and an endoscope system provided with a function of signal processing on a near-point image and a far-point image.

2. Description of the Related Art

Conventionally, endoscopes including an elongated insertion portion have been widely used in a medical field or the like. Operators can observe interiors of a subject by inserting an insertion portion into the subject and causing a display apparatus to display an endoscopic image inside the subject. The endoscopic image displayed on the display apparatus is adjusted to appropriate brightness by controlling an illumination light quantity or aperture based on brightness of an acquired endoscopic image.

Furthermore, in recent years, endoscopes capable of performing near-point observation have also been proposed in addition to normal observation. Near-point observation picks up images of a subject at a near point and enables observation with a region of the subject enlarged. Regarding dimming control of a near-point image, for instance, International Publication No. 2013/180147 proposes an endoscope apparatus that controls aperture so as to increase the magnitude of aperture opening as much as possible when a distance from the subject is small and sufficient brightness can be obtained.

Since a near-point image is generally an image obtained when a distal end portion of the insertion portion approaches the subject, there is a problem that a light distribution of illumination light in the endoscopic image becomes uneven. For instance, illumination ranges of illumination light beams radiated from two illumination windows overlap when a subject is away from the distal end portion of the insertion portion. Meanwhile, when a subject is close to the distal end portion, there can be some areas not exposed to direct illumination light, which may result in light distribution unevenness in the endoscopic image.

In a normal observation mode, not in a near-point observation mode, an inner region such as a lumen in an endoscopic image may appear completely dark. There is a method for increasing brightness of the dark region by detecting, from the endoscopic image, pixels in the dark region having pixel values lower than a predetermined threshold and increasing only the pixel values of the pixels in the dark region by a predetermined gain.

Using such a method for increasing brightness of the image of the dark region in the endoscopic image, it may also be possible to increase the pixel values of the pixels of the dark region not exposed to direct illumination light in the aforementioned near-point image.

SUMMARY OF THE INVENTION

An endoscopic image processing apparatus according to one aspect of the present invention is an endoscopic image processing apparatus that applies signal processing to a near-point image picked up at a near point with respect to a subject and a far-point image picked up at a far point with respect to the subject, the apparatus including a memory configured to store a first threshold for determining a first dark region in the near-point image inputted, a brightness correction circuit configured to perform first brightness correction on the near-point image based on the first threshold depending on timing of acquiring the near-point image and perform second brightness correction on the far-point image based on a second threshold depending on timing of acquiring the far-point image, and a light distribution state determination circuit configured to determine, based on reference near-point image data including light distribution information acquired from the endoscope coupled with the endoscopic image processing apparatus, whether a light distribution state of a live image from the endoscope inputted to the brightness correction circuit is a light distribution state of the near-point image. The brightness correction circuit, in the timing of acquiring the near-point image, performs the first brightness correction when the light distribution state determination circuit determines that the light distribution state of the live image is the light distribution state of the near-point image, and does not perform the first brightness correction or performs the second brightness correction based on the second threshold when the light distribution state determination circuit determines that the light distribution state of the live image is not the light distribution state of the near-point image.

An endoscope system according to another aspect of the present invention includes the endoscopic image processing apparatus according to one aspect and an endoscope configured to acquire the near-point image and the far-point image.

DETAILED DESCRIPTION OF THE PREFERRED EMBODIMENTS

Hereinafter, embodiments of the present invention will be described with reference to the accompanying drawings.

First Embodiment

Figure 1:
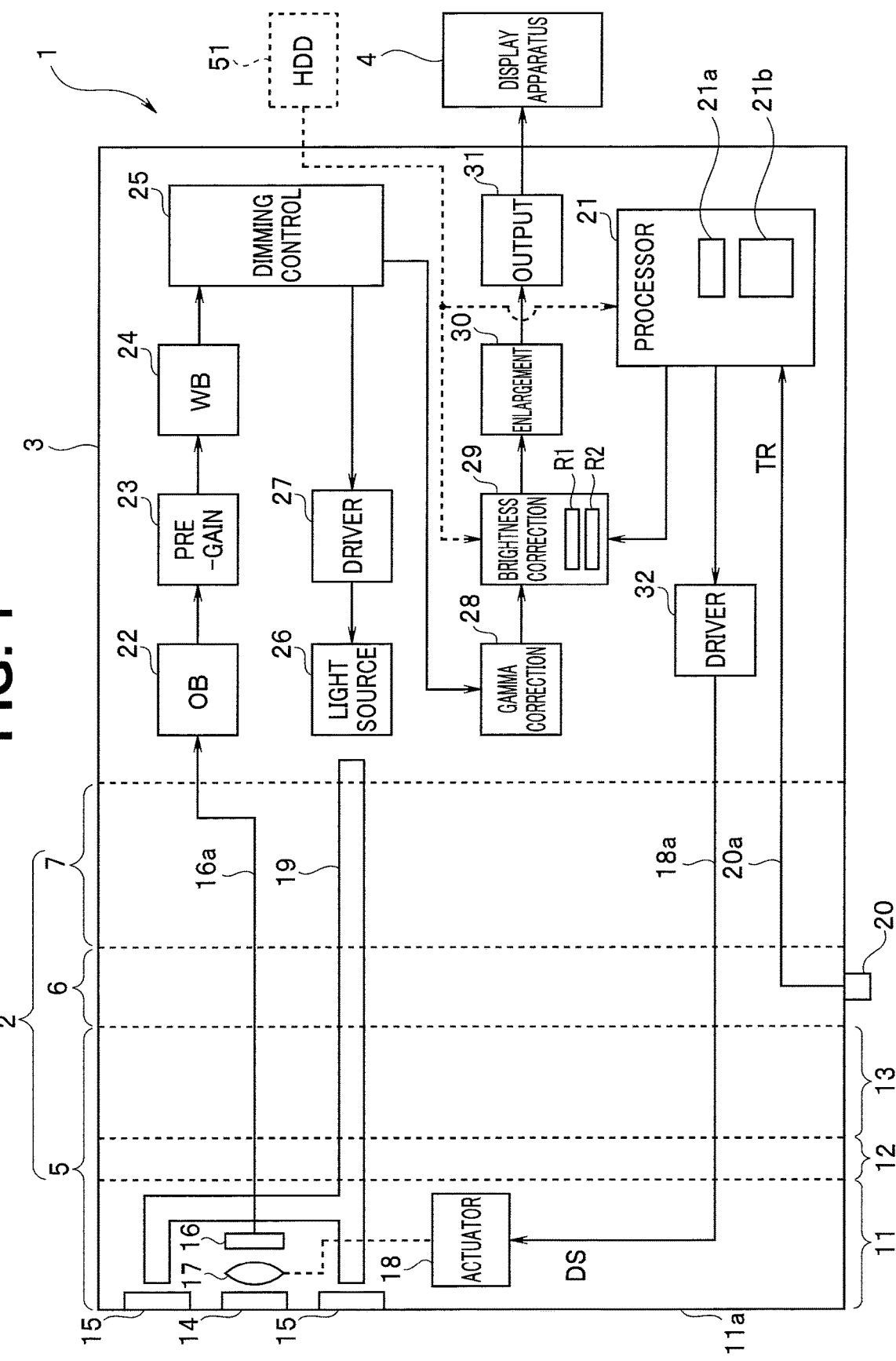
FIG. 1 is a configuration diagram illustrating a schematic configuration of an endoscope apparatus according to a first embodiment of the present invention.

FIG. 1 is a configuration diagram illustrating a schematic configuration of an endoscope apparatus according to an embodiment of the present invention.

An endoscope apparatus 1 is an endoscope system including an endoscope 2, a main body apparatus 3 and a display apparatus 4.

The endoscope 2 includes an elongated insertion portion 5, an operation portion 6 with which a proximal end of the insertion portion 5 is coupled and a cable 7 that extends from the operation portion 6. The endoscope 2 is coupled with the main body apparatus 3 via a connector provided at a proximal end portion of the cable 7.

The insertion portion 5 includes a distal end portion 11, a bending portion 12 and a flexible tube portion 13 in order from the distal end.

The distal end portion 11 includes an observation window 14 and two illumination windows 15. An objective optical system and an image pickup device 16 are disposed behind the observation window 14. A plurality of signal lines coupled with the image pickup device 16 are inserted in the bending portion 12 and the flexible tube portion 13. Note that FIG. 1 illustrates only a signal line 16a for transmitting an image pickup signal from among a plurality of signal lines of the image pickup device 16.

The two illumination windows 15 are disposed on a distal end face 11a of the distal end portion 11 so as to sandwich the observation window 14. White illumination light from the two illumination windows 15 is emitted so as to spread parallel to an optical axis of the objective optical system, and so an observation region of the subject is illuminated substantially uniformly.

As will be described later, the endoscope apparatus 1 includes a far-point observation mode and a near-point observation mode. The far-point observation mode is a so-called normal observation mode. The "far point" here means a middle-to-far point. An endoscopic image obtained in the far-point observation mode is a far-point image picked up at a far point with respect to the subject. An endoscopic image obtained in the near-point observation mode is a near-point image picked up at a near point with respect to the subject.

Thus, the main body apparatus 3 is an endoscopic image processing apparatus that applies signal processing to a near-point image picked up at a near point with respect to the subject and to a far-point image picked up at a far point with respect to the subject.

In the far-point observation mode, since the distal end portion 11 is a predetermined distance or more away from the observation region of the subject, the two illumination ranges of two illumination light beams at the subject overlap. Therefore, the observation region of the subject is illuminated substantially uniformly.

However, in the near-point observation mode, when the distal end portion 11 approaches the observation region of the subject to less than a predetermined distance, the two illumination ranges of the two illumination light beams at the subject do not overlap. Thus, the observation region of the subject is not illuminated substantially uniformly. For instance, since the two illumination ranges separate from each other, a central part of the near-point image becomes dark.

Figure 2:
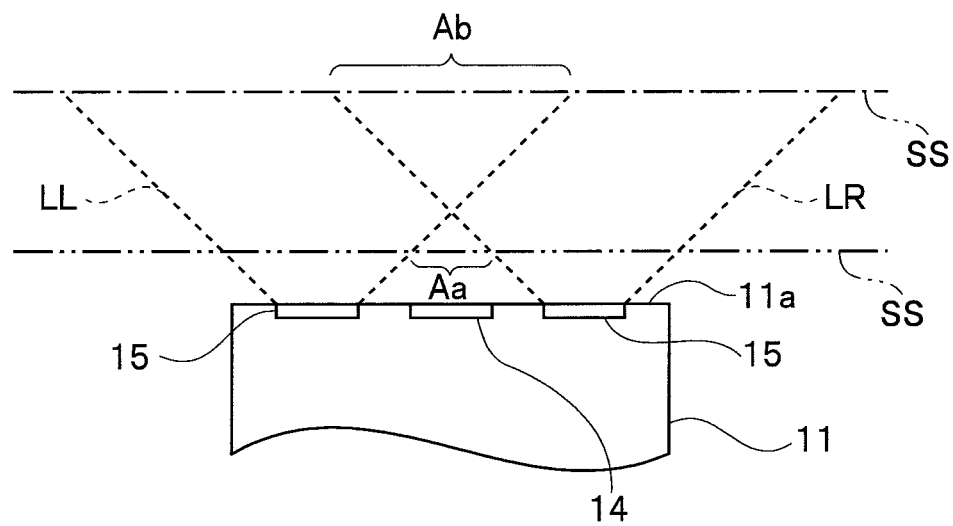
FIG. 2 is a diagram for describing illumination ranges of two illumination light beams in a near-point observation mode and a far-point observation mode according to the first embodiment of the present invention.

FIG. 2 is a diagram for describing illumination ranges of the two illumination light beams in the near-point observation mode and the far-point observation mode.

In the far-point observation mode, as shown by a single-dot dashed line, since a surface SS of the subject is far from the distal end face 11a of the distal end portion 11, an overlapping region Ab is generated between illumination ranges LR and LL of the two illumination light beams emitted from the two illumination windows 15.

In the near-point observation mode, as shown by a two-dot dashed line, since the surface SS of the subject is near the distal end face 11a of the distal end portion 11, a region Aa may be generated where the illumination ranges LR and LL of the two illumination light beams emitted from the two illumination windows 15 do not overlap.

Thus, the near-point image may include a dark region resulting from the region Aa where the illumination ranges LR and LL of the two illumination light beams do not overlap.

The objective optical system can be switched between two focal positions of the near point and the far point.

FIG. 1 illustrates only a movable lens 17 configured to move on the optical axis when the two focal positions are switched. As shown by a dotted line, the movable lens 17 is coupled with an actuator 18 and is caused to move to the near point position or the far point position by the actuator 18 provided in the distal end portion 11.

The actuator 18 includes, for instance, a voice coil motor. A signal line 18a coupled with the actuator 18 is inserted in the bending portion 12 and the flexible tube portion 13, and coupled with the main body apparatus 3. The actuator 18 is driven by a drive signal DS from the main body apparatus 3.

A distal end face of a light guide 19 is disposed behind each illumination window 15. The light guide 19 is inserted in the endoscope 2. Light emitted from a light source apparatus, which will be described later, is incident on a proximal end face of the light guide 19. The distal end portion of the light guide 19 is branched into two portions and illumination light is emitted from the distal end face of each branch section toward each illumination window 15.

The bending portion 12 includes a plurality of bending pieces that are not shown, and the distal end portion 11 can be curved in up-down, left-right directions when a plurality of curved wires inserted in the flexible tube portion 13 are pulled or relaxed in response to operation of two bending operation knobs (not shown) provided at the operation portion 6.

A plurality of buttons to be operated by a user such as an operator are disposed at the operation portion 6. FIG. 1 illustrates only a switchover button 20 configured to switch between the near-point observation mode and the far-point observation mode from among the plurality of buttons. When the switchover button 20 is in the near-point observation mode, the focal position of the objective optical system becomes the near point, whereas when the switchover button 20 is in the far-point observation mode, the focal position of the objective optical system becomes a far point, a middle-to-far point here.

A signal line 20a coupled with the switchover button 20 is coupled with the main body apparatus 3, and a switchover signal TR of the switchover button 20 to be operated by the user is supplied to a processor 21 of the main body apparatus 3. The processor 21 determines timing of acquiring a near-point image and timing of acquiring a far-point image based on a signal from the endoscope 2 that acquires the near-point image and the far-point image, the switchover signal TR, here.

A time or a period at or during which the switchover button 20 is in a near-point observation mode state is the timing of acquiring a near-point image in the endoscope apparatus 1 and a time or a period at or during which the switchover button 20 is in a far-point observation mode state is the timing of acquiring a far-point image in the endoscope apparatus 1.

The main body apparatus 3, which is a so-called video processor, includes the processor 21, an optical black (OB) circuit 22, a pre-gain circuit 23, a white balance (WB) circuit 24, a dimming control circuit 25, a light source 26, a driver 27, a gamma correction circuit 28, a brightness correction circuit 29, an enlargement circuit 30, an output circuit 31 and a driver 32.

The main body apparatus 3 is an endoscopic image processing apparatus configured to process an image pickup signal from the endoscope 2, generate an endoscopic image and output the endoscopic image to the display apparatus 4.

The processor 21 includes hardware circuits such as a central processing unit (hereinafter referred to as a "CPU") 21a and a memory 21b. The memory 21b includes a ROM, a RAM or the like. The CPU 21a implements various functions of the endoscope apparatus 1 by executing various control programs stored in the ROM.

Note that the processor 21 may be constructed of an integrated circuit such as an FPGA (field programmable gate array).

The ROM stores, as default, threshold TH data used for brightness correction, which will be described later, and gain G data, which will be described later, in advance. Here, a threshold THn and a gain Gn for near-point observation, and a threshold THf and a gain Gf for far-point observation are stored in the ROM as the threshold TH and the gain G.

As will be described later, the threshold THn is used to determine a dark region in the near-point image and the threshold THf is used to determine a dark region in the far-point image. Therefore, the memory 21b constitutes a storage unit that stores the threshold THn and the gain Gn to determine the dark region in the inputted near-point image and the threshold THf and the gain Gf to determine the dark region in the inputted far-point image.

The settings of the threshold TH and the gain G can be changed by the user and the data, settings of which have been changed, is stored in the RAM or in a non-volatile rewritable memory such as a flash memory (not shown) or the like.

Figure 3:
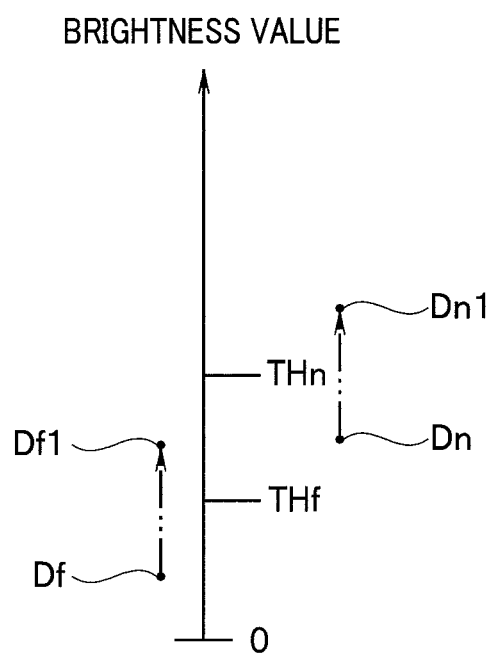
FIG. 3 is a diagram for describing a magnitude relationship between a threshold for a near-point observation mode and a threshold for a far-point observation mode according to the first embodiment of the present invention.

FIG. 3 is a diagram for describing a magnitude relationship between the threshold THn for the near-point observation mode and the threshold THf for the far-point observation mode.

In FIG. 3, a vertical axis represents a brightness value. When the brightness value takes a value within a range of 0 to 255, for instance, the threshold THn for the near-point observation mode takes a value larger than the threshold THf for the far-point observation mode, that is, a brighter value. In other words, the threshold THf is smaller than the threshold THn.

When a pixel value of a pixel in the near-point image is equal to or less than the threshold THn, the brightness correction circuit 29 corrects the pixel value of the pixel to a value multiplied by the gain Gn. A value Dn shown as an instance in FIG. 3 is corrected to a value Dn1. In other words, the brightness correction circuit 29 corrects the brightness of the near-point image using the gain Gn so that the dark region of the near-point image becomes brighter.

When a pixel value of a pixel in the far-point image is equal to or less than the threshold THf, the brightness correction circuit 29 corrects the pixel value of the pixel to a value multiplied by the gain Gf. The value Df shown as an instance in FIG. 3 is corrected to a value Df1. In other words, the brightness correction circuit 29 corrects the brightness of the far-point image using the gain Gf so that the dark region of the far-point image becomes brighter.

Thus, in the near-point image, not only pixel values of pixels equal to or less than the threshold THf are corrected by the gain Gn, but also pixel values of pixels exceeding the threshold THf and less than the threshold THn are corrected by the gain Gn.

Note that the gains Gn and Gf are preferably values at which noise is inconspicuous level in the near-point image and the far-point image, brightness of which has been corrected.

Returning to FIG. 1, the optical black (OB) circuit 22 is a circuit configured to receive an image pickup signal from the image pickup device 16 and perform optical black clamp processing or the like on the image pickup signal.

The pre-gain circuit 23 is configured to perform gain adjustment on the signal outputted from the optical black (OB) circuit 22.

The white balance (WB) circuit 24 is configured to perform white balance processing on the signal outputted from the pre-gain circuit 23.

The dimming control circuit 25 is configured to control the driver 27 for the light source 26 based on the image signal from the white balance (WB) circuit 24 and perform dimming control.

The light source 26 includes a light-emitting device such as a light-emitting diode and is configured to emit illumination light of white light.

The driver 27 is a circuit configured to output a drive current to be supplied to the light-emitting device of the light source 26.

The gamma correction circuit 28 is configured to perform gamma correction processing on the image signal outputted via the dimming control circuit 25. In other words, the gamma correction circuit 28 is configured to output an image signal of a live image LG of the subject obtained by the image pickup device 16.

The brightness correction circuit 29 is configured to correct brightness of the live image LG. The brightness correction circuit 29 incorporates two registers R1 and R2. Data of the threshold TH is set in the register R1. Data of the gain G is set in the register R2. Data of the threshold TH and the gain G set in the registers R1 and R2 is written by the processor 21.

Data of each pixel obtained by scanning the gamma-corrected live image LG is serially inputted to the brightness correction circuit 29.

The brightness correction circuit 29 is configured to compare a pixel value of each pixel of a plurality of serially inputted pixels with the threshold TH stored in the register R1 and correct, when the pixel value is equal to or less than the threshold TH, the pixel value using the gain G stored in the register R2 so as to increase the pixel value. When the pixel value is not equal to or less than the threshold TH, the brightness correction circuit 29 does not correct the pixel value.

The enlargement circuit 30 is a scaling circuit configured to adjust the size of the live image LG so as to appropriately display the live image LG on the display apparatus 4.

The output circuit 31 is a circuit configured to output the image signal outputted from the enlargement circuit 30 to the display apparatus 4.

The processor 21 is configured to monitor the switchover signal TR of the switchover button 20, output a control signal to the driver 32 when the switchover button 20 is switched from the far-point observation mode to the near-point observation mode, output a drive signal DS to the signal line 18a and move the movable lens 17 to the near point position.

When the switchover button 20 is switched from the far-point observation mode to the near-point observation mode, the processor 21 outputs a control signal to the driver 32, outputs a drive signal DS to the signal line 18a and moves the movable lens 17 to the far point position.

Furthermore, when the switchover button 20 is switched from the far-point observation mode to the near-point observation mode, the processor 21 reads the threshold THn and the gain Gn for near-point observation stored in the ROM or RAM and writes the threshold THn and the gain Gn in the registers R1 and R2 of the brightness correction circuit 29, respectively.

When the switchover button 20 is switched from the far-point observation mode to the near-point observation mode, the processor 21 reads the threshold THf and the gain Gf for far-point observation stored in the ROM or RAM and writes the threshold THf and the gain Gf in the registers R1 and R2 of the brightness correction circuit 29, respectively.

(Operation)

Next, operation of the aforementioned endoscope apparatus 1 will be described. When the operator inserts the insertion portion 5 into the subject, an endoscopic image inside the subject, that is, the live image LG is displayed on the display apparatus 4.

While watching the live image LG, the operator operates the switchover button 20 if necessary, and can thereby move the movable lens 17 of the objective optical system to the near point position or the far point position to perform an endoscopic inspection.

Here, only the brightness correction processing when switchover between the near-point observation mode and the far-point observation mode takes place will be described.

The processor 21 can determine whether the user has selected the far-point observation mode or the near-point observation mode based on the switchover signal TR of the switchover button 20.

At startup of the endoscope apparatus 1, the processor 21 reads the threshold THf and the gain Gf in the far-point observation mode or the threshold THn and the gain Gn in the near-point observation mode stored in the memory 21b, and writes the thresholds and the gains in the registers R1 and R2 of the brightness correction circuit 29.

For instance, if the far-point observation mode is selected, at startup of the endoscope apparatus 1, the processor 21 controls the driver 32 to drive the actuator 18 and cause the movable lens 17 of the objective optical system to move to the far point position.

At the same time, if the far-point observation mode is selected, the processor 21 reads the data of the threshold THf and the gain Gf for the far-point observation mode stored in the memory 21b and sets the threshold THf and the gain Gf in the registers R1 and R2 of the brightness correction circuit 29, respectively. Thus the processor 21 constitutes a threshold setting section configured to set the threshold THf in the register R1 based on the timing of acquiring the far-point image, or more specifically, at timing of switchover to the far-point image mode of the switchover button 20.

In the far-point observation mode, the brightness correction circuit 29 compares a pixel value of each pixel of the image signal of the live image LG outputted from the gamma correction circuit 28 with the threshold THf stored in the register R1.

When the pixel value is equal to or less than the threshold THf, the brightness correction circuit 29 corrects the pixel value using the gain Gf stored in the register R2. For instance, the gain Gf is a coefficient value and the pixel value is corrected by multiplying the pixel value by the gain Gf.

Figure 4:
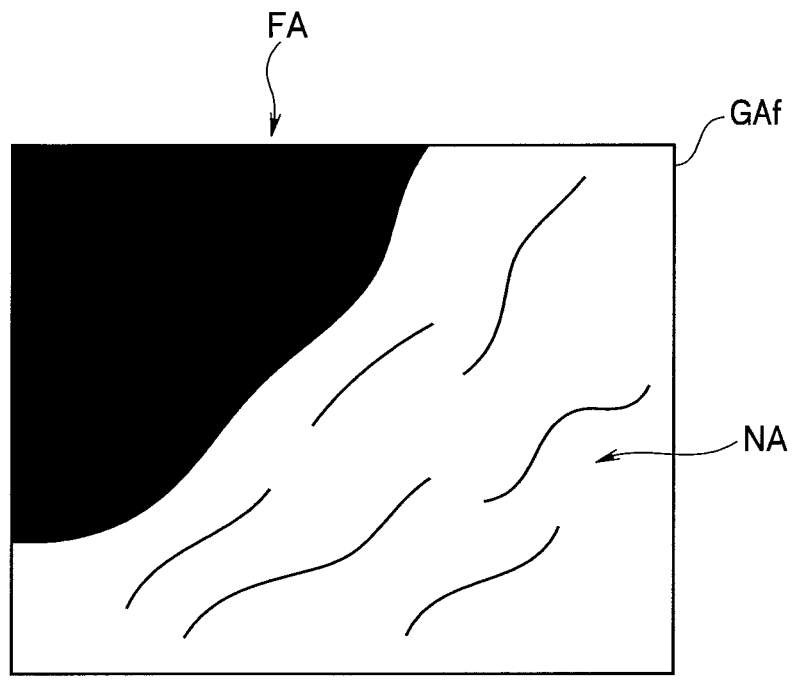
FIG. 4 is a schematic view illustrating an instance of a far-point image when the brightness correction circuit does not perform brightness correction according to the first embodiment of the present invention.

FIG. 4 is a schematic view illustrating an instance of a far-point image when the brightness correction circuit 29 does not perform brightness correction.

A far-point image GAf is an image picked up at a far point with respect to the subject. In FIG. 4, since the distal end portion 11 is oriented toward the back of the lumen, an endoscopic image GAf, which is the far-point image, is displayed brightly in a region NA of an inner wall region near the distal end portion 11, whereas a region FA in the back of the lumen is displayed completely black.

Figure 5:
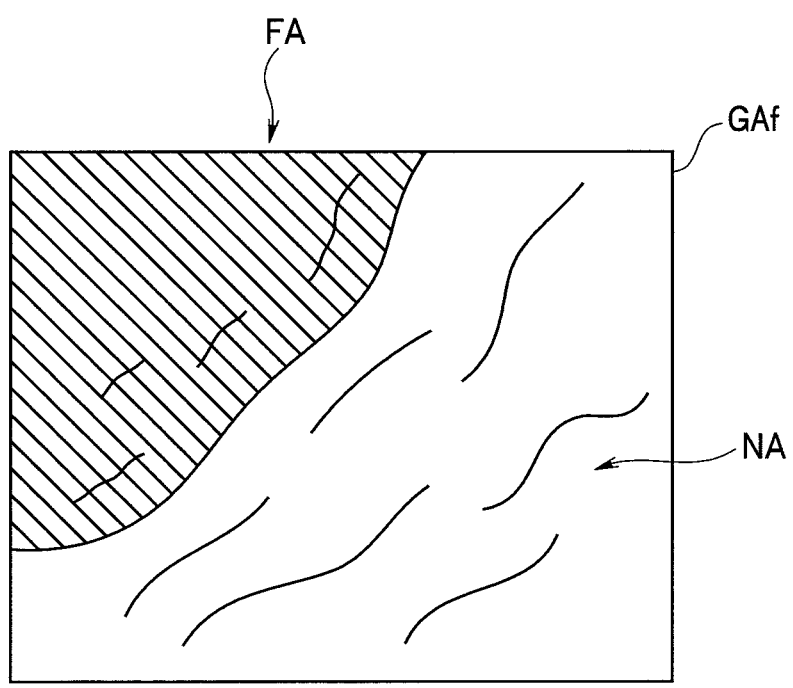
FIG. 5 is a schematic view illustrating an instance of a far-point image when the brightness correction circuit performs brightness correction according to the first embodiment of the present invention.

FIG. 5 is a schematic view illustrating an instance of a far-point image when the brightness correction circuit 29 performs brightness correction.

As described above, the brightness correction circuit 29 corrects, using the gain Gf, a pixel having a pixel value equal to or less than the threshold THf. The threshold THf is a value of the level to determine brightness (or darkness) of, for instance, the region FA in the back of the lumen in the far-point observation mode.

The region FA in the back of the lumen is displayed completely black before the correction, but the brightness correction circuit 29 causes the region FA in the back of the lumen, which is displayed completely black in FIG. 4, to be displayed somewhat brighter as shown by shading in FIG. 5.

Since the region FA in the back in the far-point observation mode becomes somewhat brighter as illustrated in FIG. 5, the user can have a depth feeling in the far-point image GAf.

When the switchover button 20 is switched from the far-point observation mode to the near-point observation mode, the processor 21 controls the driver 32 to drive the actuator 18 and cause the movable lens 17 of the objective optical system to move to the near-point position.

When the near-point observation mode is selected at the same time, the processor 21 reads the threshold THn and the gain Gn for the near-point observation mode stored in the memory 21b and sets the threshold THn and the gain Gn in the registers R1 and R2 of the brightness correction circuit 29, respectively. Thus, the processor 21 constitutes a threshold setting section configured to set the threshold THn in the register R1 according to the timing of acquiring the near-point image, or more specifically, at timing of switchover to the near-point image mode of the switchover button 20.

In the near-point observation mode, the brightness correction circuit 29 compares a pixel value of each pixel of the image signal of the live image LG outputted from the gamma correction circuit 28 with the threshold THn stored in the register R1.

When the pixel value is equal to or less than the threshold THn, the brightness correction circuit 29 corrects the pixel value using the gain Gn stored in the register R2. For instance, the gain Gn is a coefficient value and the pixel value is corrected by multiplying the pixel value by the gain Gn.

Note that the observation mode here is switched to any one of the two observation modes by the switchover button 20, but the observation mode may be made settable by a push button. A time or a period at or during which the push button is depressed is the timing of acquiring the near-point image. A time or a period at or during which the push button is not depressed is the timing of acquiring the far-point image.

In other words, a push button for the near-point observation mode may be provided instead of the switchover button 20 and the brightness correction circuit 29 may be configured to perform brightness correction using the threshold THn and the gain Gn for near-point observation only while the push button is depressed and perform brightness correction using the threshold THf and the gain Gf for far-point observation while the push button for the near-point observation mode is not depressed.

Figure 6:
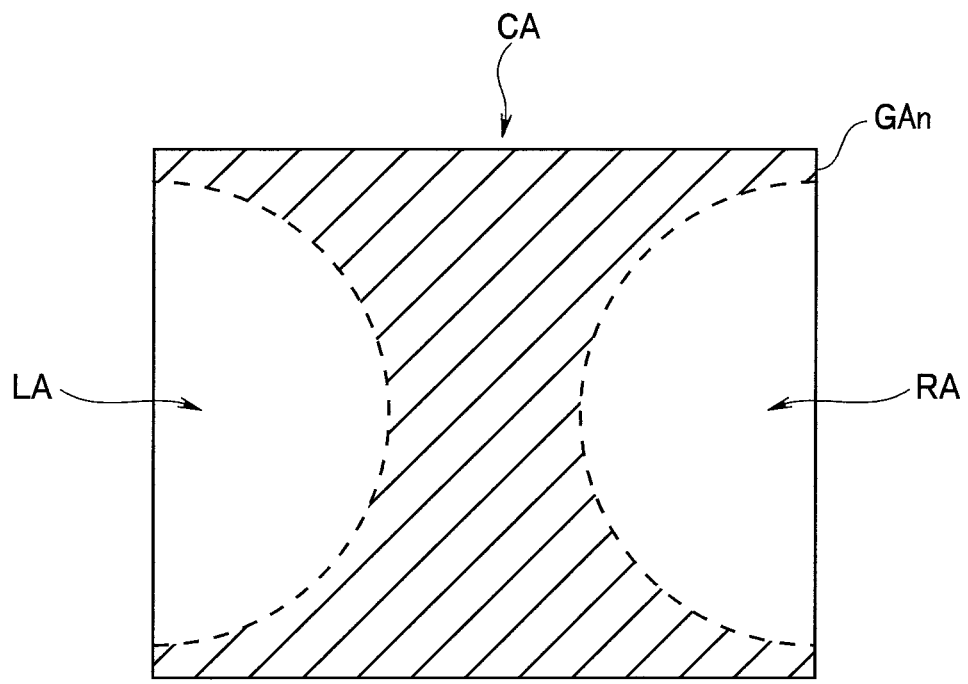
FIG. 6 is a schematic view illustrating an instance of a near-point image when the brightness correction circuit does not perform brightness correction according to the first embodiment of the present invention.

FIG. 6 is a schematic view illustrating an instance of a near-point image when the brightness correction circuit 29 does not perform brightness correction.

A near-point image is an image picked up at a near point with respect to the subject. In FIG. 6, the distal end portion 11 is directed toward the inner wall of the lumen and located near the inner wall, and so a region CA of a central part of an endoscopic image GAn, which is a near-point image, becomes dark as shown by diagonal lines with narrow line interval. Thus, regions RA and LA of regions exposed to illumination light from each illumination window 15 are displayed brightly, whereas the region CA of the central part of the endoscopic image GAn, which is the near-point image, becomes somewhat dark.

Figure 7:
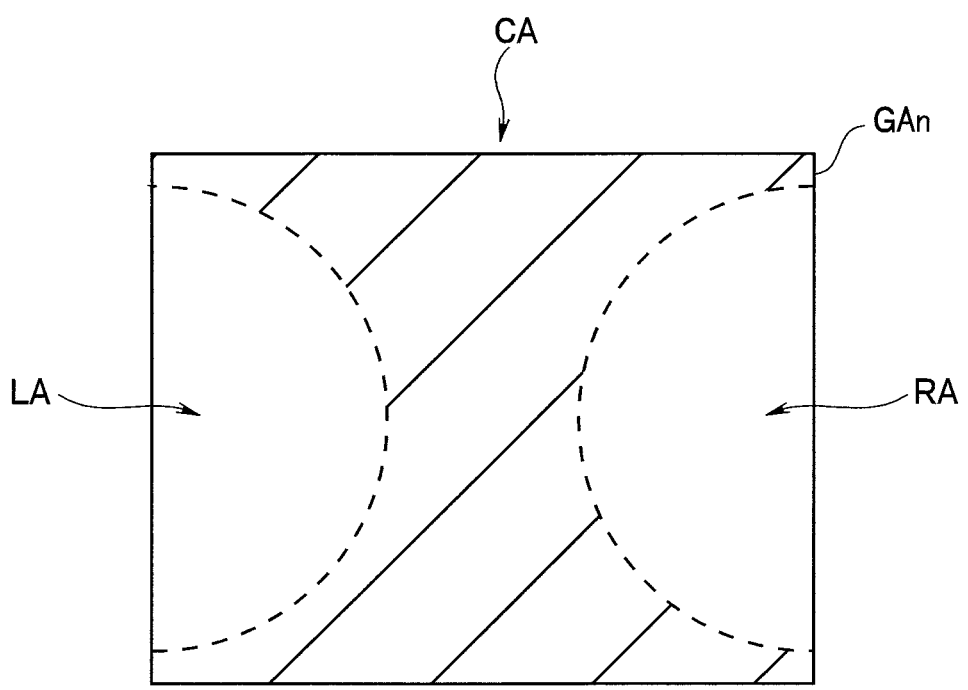
FIG. 7 is a schematic view illustrating an instance of a near-point image when the brightness correction circuit performs brightness correction according to the first embodiment of the present invention.

FIG. 7 is a schematic view illustrating an instance of the near-point image when the brightness correction circuit 29 performs brightness correction.

As described above, the brightness correction circuit 29 corrects, using the gain Gf, pixels having pixel values equal to or less than the threshold THn. The threshold THn is a value of the level to determine brightness (or darkness) of, for instance, the region CA of the central part not directly exposed to illumination light in the near-point observation mode.

Thus, for instance, the region CA of the central part is displayed somewhat dark before the correction, but the brightness correction circuit 29 causes the region CA, which is displayed somewhat dark in FIG. 6, to be displayed somewhat brighter as illustrated in FIG. 7. In FIG. 7, the region CA in the central part is shown by diagonal lines with larger line interval than the diagonal lines in FIG. 6. As a result, the light distribution unevenness in the near-point image is reduced, making it easier for the user to view the endoscopic image GAn.

As described so far, the brightness correction circuit 29 as a brightness correction section performs brightness correction on the near-point image at timing of acquiring the near-point image, that is, according to the switchover signal TR of the switchover button 20 or an on signal of the push button and based on the threshold THn. Furthermore, the brightness correction circuit 29 performs brightness correction on the far-point image at timing of acquiring the far-point image, that is, according to the switchover signal TR of the switchover button 20 or a non-on signal of the push button and based on the threshold THf.

As described above, according to the aforementioned embodiment, the threshold TH differs between the far-point observation mode and the near-point observation mode, and the threshold THn in the near-point observation mode is larger than the threshold THf in the far-point observation mode, and so the region of the near-point image that is displayed somewhat dark is displayed somewhat bright, and as a result, the light distribution unevenness of the near-point image is reduced.

Second Embodiment

In the first embodiment, while the observation mode is set to the near-point observation mode, brightness correction is performed using the threshold THn and the gain Gn for the near-point observation mode. In the second embodiment, while the observation mode is the near-point observation mode, a light distribution state of an endoscopic image is determined, and if the light distribution state is a light distribution state of the near-point image, brightness correction is performed, whereas if the light distribution state is not the light distribution state of the near-point image, brightness correction is not performed.

Since a configuration of an endoscope apparatus of the second embodiment is substantially the same as the configuration of the endoscope apparatus of the first embodiment, description of the same components will be omitted and only different components will be described.

Figure 8:
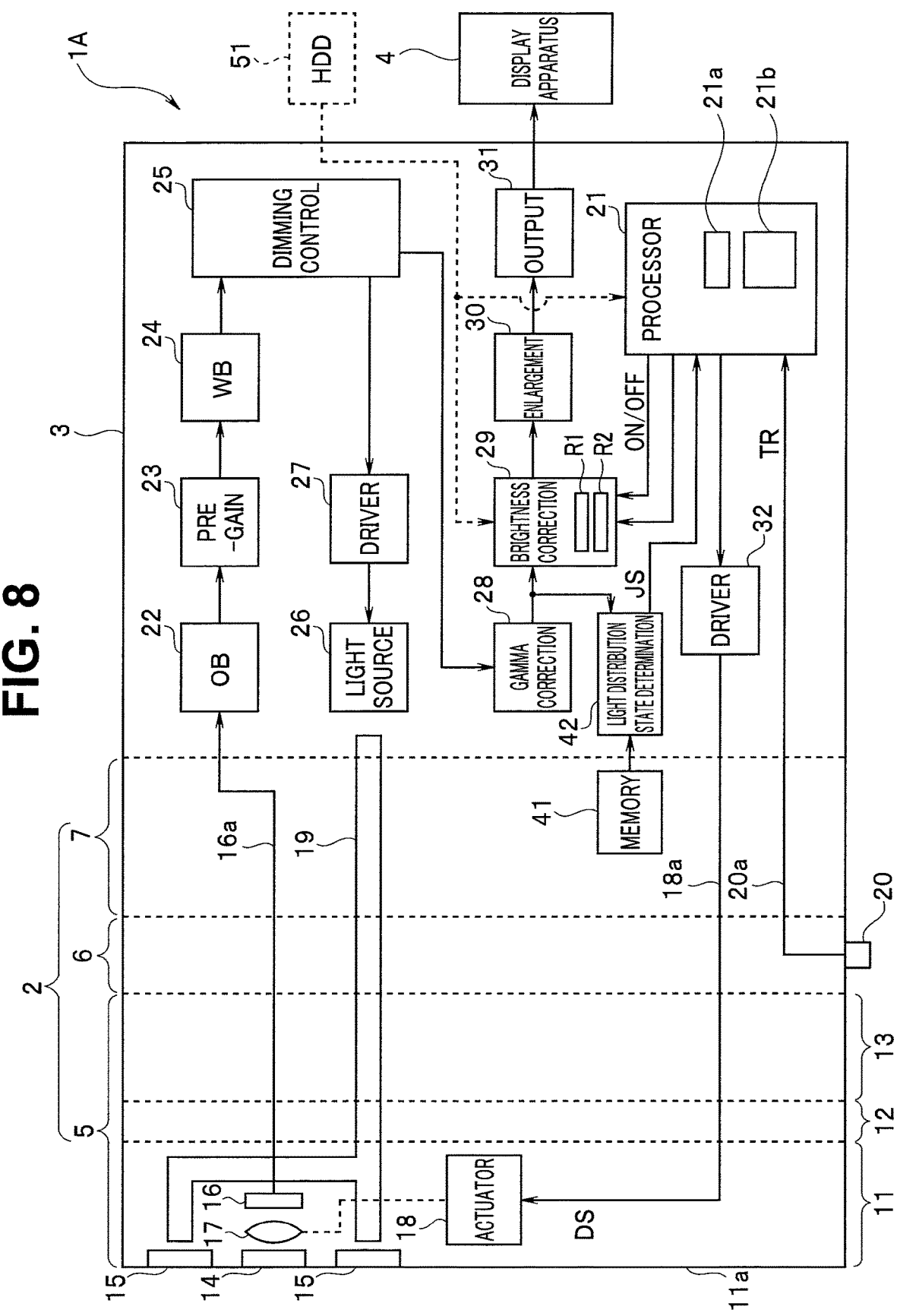
FIG. 8 is a configuration diagram illustrating a schematic configuration of an endoscope apparatus according to a second embodiment of the present invention.

FIG. 8 is a configuration diagram illustrating a schematic configuration of the endoscope apparatus according to the present embodiment.

The endoscope 2 of an endoscope apparatus 1A according to the present embodiment includes a non-volatile memory 41 such as a flash memory. Here, the memory 41 is incorporated in a connector provided, for instance, at a proximal end portion of the cable 7.

The memory 41 stores image data of near-point image (hereinafter referred to as a "reference near-point image") RNG, which is referred to as reference data when a light distribution state is determined.

Arrangements of the observation window at the distal end portion 11 of the insertion portion 5 and the two illumination windows, and the light emission range of each illumination light or the like differ depending on the type of endoscope or the like. Therefore, the image data of the reference near-point image RNG stored in the memory 41 includes information on light distribution unevenness of the near-point image of the endoscope.

For instance, image data of an average image of a near-point image obtained when the endoscope is set to the near-point observation mode and an image of the subject is picked up at a near point is stored in the memory 41 as the reference near-point image RNG.

Note that the image data of the reference near-point image RNG may be image data of an endoscopic image obtained by actually picking up an image in the near-point observation mode using the endoscope or may be image data created by simulation using a computer.

The main body apparatus 3 includes a light distribution state determination circuit 42. When a connector of the cable 7 of the endoscope 2 is coupled with the main body apparatus 3, the light distribution state determination circuit 42 can read the image data of the reference near-point image RNG from the memory 41.

The light distribution state determination circuit 42 determines whether or not the live image LG outputted from the gamma correction circuit 28 is a near-point image based on the reference near-point image RNG and outputs a determination result signal JS to the processor 21. The determination result signal JS shows whether or not the light distribution state of the endoscopic image obtained by the image pickup device 16 is a light distribution state of the near-point image.

In other words, the light distribution state determination circuit 42 constitutes a light distribution state determination section configured to determine whether the light distribution state of a live image from the endoscope 2 inputted to the brightness correction circuit 29 is a light distribution state of a near-point image based on the light distribution information acquired from the endoscope 2 coupled with the main body apparatus 3.

For instance, the light distribution state determination circuit 42 compares the live image LG from the gamma correction circuit 28 with the reference near-point image RNG from the memory 41 for each pixel, calculates a difference in pixel values and calculates the sum of differences of all pixels.

When the calculated sum is equal to or less than a predetermined value, the light distribution state determination circuit 42 determines that the live image LG from the gamma correction circuit 28 is a near-point image and outputs a determination result signal JS of "1" to the processor 21.

When the calculated sum is not equal to or less than the predetermined value, the light distribution state determination circuit 42 determines that the live image LG from the gamma correction circuit 28 is not a near-point image and outputs a determination result signal JS of "0" to the processor 21.

In the near-point observation mode, when the distal end face 11a of the distal end portion 11 is made to face and approach the surface of the subject, the live image LG has a light distribution as illustrated in FIG. 6. Image data of an image such as the image in FIG. 6 is stored in the memory 41 as the reference near-point image RNG.

Thus, when the live image LG from the gamma correction circuit 28 has a light distribution similar to the light distribution of the image in FIG. 6, the calculated sum becomes equal to or less than a predetermined value.

However, while the observation mode is set to the near-point observation mode, the user may direct the distal end portion 11 toward the back of the lumen. In such a case, the live image LG becomes an image as illustrated in FIG. 4. Thus, the image as illustrated in FIG. 4 is significantly different in the light distribution from the image as illustrated in FIG. 6, and so the sum calculated in the light distribution state determination circuit 42 exceeds a predetermined value.

Note that the live image LG may be divided into a plurality of predetermined regions, the reference near-point image RNG may also be divided into a plurality of regions as with the live image LG, and the light distribution state determination circuit 42 may compare average values of brightness values for each divided region in the live image LG and the reference near-point image RNG and determine whether or not the live image LG is a near-point image based on the number of regions where a difference in the respective average values is equal to or less than a predetermined value or the ratio of the number of regions where a difference in the respective average values is equal to or less than the predetermined value to the total number of divided regions.

When the determination result signal JS is "1," the processor 21 outputs an on signal (ON) that enables brightness correction to the brightness correction circuit 29. When the determination result signal JS is "0," the processor 21 outputs an off signal (OFF) that disables brightness correction to the brightness correction circuit 29.

While receiving an on signal (ON), the brightness correction circuit 29 performs brightness correction. While receiving an off signal (OFF), the brightness correction circuit 29 does not perform brightness correction. In other words, the brightness correction circuit 29 performs brightness correction when the light distribution state determination circuit 42 determines that the light distribution state of the live image LG is a light distribution state of a near-point image, and does not perform brightness correction when the light distribution state determination circuit 42 determines that the light distribution state of the live image LG is not a light distribution state of a near-point image.

Therefore, when the user sets the endoscope apparatus 1A to the near-point observation mode by operating the switchover button 20, if the light distribution state of the obtained live image LG is not similar to the light distribution state of the reference near-point image RNG, the processor 21 outputs an off signal (OFF) to the brightness correction circuit 29. As a result, the brightness correction circuit 29 does not perform brightness correction.

For instance, when the user sets the endoscope apparatus 1A to the near-point observation mode, if the live image LG has a light distribution state of the image as illustrated in FIG. 6, the brightness correction circuit 29 receives an on signal (ON), and so the brightness correction circuit 29 performs brightness correction using the threshold THn and the gain Gn for the near-point observation mode. As a result, the endoscopic image as illustrated in FIG. 7 is displayed on the display apparatus 4.

When the user sets the endoscope apparatus 1A to the near-point observation mode, if the user directs the distal end portion 11 toward the back of the lumen and the live image LG is in a light distribution state of the image as illustrated in FIG. 4, the brightness correction circuit 29 receives an off signal (OFF), and so the brightness correction circuit 29 does not perform brightness correction using the threshold THn and the gain Gn for the near-point observation mode or performs brightness correction using the threshold THf and the gain Gf for the far-point observation mode. As a result, the image as illustrated in FIG. 6 or FIG. 7 is displayed on the display apparatus 4.

Note that when the brightness correction circuit 29 receives an off signal (OFF) in the near-point observation mode, the user may be able to set whether brightness correction is not performed on the live image LG or brightness correction is performed using the threshold THf and the gain Gf for far-point observation. In that case, setting information as to whether or not to perform brightness correction set by the user is stored in the RAM of the memory 21b and referred to by the brightness correction circuit 29.

Note that operation in the far-point observation mode is the same as the operation in the far-point observation mode in the first embodiment.

Thus, according to the aforementioned second embodiment, the same effects as the effects of the first embodiment are obtained, and brightness correction for the near-point observation mode is automatically performed only when the live image has a light distribution state of the near-point image in the near-point observation mode.

As described so far, according to the first and second embodiments, it is possible to provide an endoscopic image processing apparatus and an endoscope system capable of reducing light distribution unevenness of a near-point image in an endoscopic image processing apparatus configured to perform signal processing on a near-point image and a far-point image.

Note that although the aforementioned two embodiments are applied to an endoscope apparatus configured to perform so-called normal light observation using white light as illumination light, the aforementioned two embodiments are also applicable to an endoscope apparatus configured to perform special light observation using narrow-band light.

For instance, there is an endoscope apparatus capable of observing micro blood vessel structure or the like using narrow-band light having a central wavelength of 415 nm and 540 nm and a full width at half maximum of 10 nm. When such an endoscope apparatus has a near-point observation mode and a far-point observation mode, the aforementioned two embodiments are applicable to such an endoscope apparatus.

Furthermore, although brightness correction is performed on a live image LG obtained by the endoscope according to the aforementioned two embodiments, brightness correction is also applicable to a recorded image of an endoscopic inspection, which has already been conducted.

For instance, when a live image LG of a video obtained by an endoscopic inspection is recorded in a storage apparatus 51 such as a hard disk drive (HDD) shown by a dotted line in FIG. 1 and FIG. 2 and information of observation mode, that is, information on timing of acquiring a near-point image and a far-point image is also recorded in the storage apparatus 51 in association with the images, it is possible to perform the brightness correction described in the aforementioned two embodiments when the recorded images are played back by inputting image signals read from the storage apparatus 51 to the processor 21 and the brightness correction circuit 29.

In other words, by recording the near-point image and the far-point image acquired by the endoscope in the storage apparatus 51 and determining the timing of acquiring the near-point image and the timing of acquiring the far-point image based on the signal stored in the storage apparatus 51 in association with the near-point image and the far-point image, it is also possible to apply the brightness correction described in the aforementioned two embodiments when the recorded endoscopic images are played back.

Next, modifications of the aforementioned two embodiments will be described.

(Modification 1)

According to the aforementioned embodiments, in the far-point observation mode, brightness correction is performed using the threshold THf and the gain Gf for far-point observation. However, in the far-point observation mode, brightness correction using the threshold THf and the gain Gf may not be performed.

In other words, brightness correction using the threshold THn and the gain Gn for near-point observation may be performed only in the near-point image observation mode, and brightness correction may not be performed when the observation mode is not the near-point observation mode.

For instance, by setting the threshold THf in the far-point observation mode to 0, it is possible to prevent brightness correction from being performed in the far-point observation mode.

Note that selection of whether or not to perform brightness correction in the far-point observation mode may be left to the user.

For instance, the operation portion 6 may be provided with a selection button so as to allow the user to select whether or not to perform brightness correction in the far-point observation mode using the selection button. When "to perform brightness correction" in the far-point observation mode is selected using the selection button, a threshold THf preset to non-zero may be used, and when "not to perform brightness correction" in the far-point observation mode is selected using the selection button, a threshold THf set to zero may be used, for instance.

Some operators may not want the dark part to be displayed brightly in the far-point observation mode, and so it is possible to respond to such requests from the operators by making whether or not to perform brightness correction selectable.

(Modification 2)

In the aforementioned two embodiments and modification 1, the processor 21 includes one threshold TH and one gain G for the near-point observation mode and the far-point observation mode, respectively. However, the processor 21 may have a plurality of thresholds TH and a plurality of gains G for at least one of the near-point observation mode and the far-point observation mode so that the user can select a desired threshold TH and a desired gain G from among them.

According to the present modification 2, since the operator can select a desired threshold TH and a desired gain G from among the plurality of thresholds TH and gains G to suit the taste of the operator, it is possible to cause the display apparatus 4 to display a live image LG for which brightness correction that suits the taste of the operator is performed.

The present invention is not limited to the aforementioned embodiments, but various changes or modifications or the like can be made without changing the gist of the present invention.

What is claimed is:

1. An endoscopic image processing apparatus comprising:
a light distribution state determination circuit configured to:
    calculate a difference in pixel value of each pixel in at least one region of a live image from an endoscope with pixel value of each pixel in at least one region of a reference near-point image;
    calculate a sum of the differences;
    determine whether the sum of the differences is equal to or less than a predetermined value;
    in response to determining that the sum of the differences is equal to or less than the predetermined value, determine that the live image is a near-point image and output a first determination result; and
    in response to determining that the sum of the differences is greater than the predetermined value, determine that the live image is not a near-point image and output a second determination result; and
a brightness correction circuit configured to:
    in response to the first determination result outputted by the light distribution state determination circuit, perform a first brightness correction on the live image using a first threshold; and
    in response to the second determination result outputted by the light distribution state determination circuit:
        not perform the first brightness correction; or perform a second brightness correction based on a second threshold.

2. The endoscopic image processing apparatus according to claim 1,
wherein the first threshold is greater than the second threshold.

3. The endoscopic image processing apparatus according to claim 1,
wherein, in performing the first brightness correction, the brightness correction circuit is configured to correct a pixel of the live image, the pixel having a pixel value equal to or less than the first threshold, using a first gain.

4. The endoscopic image processing apparatus according to claim 1,
wherein the first threshold is greater than the second threshold, and
wherein the brightness correction circuit is configured to:
in performing the first brightness correction, correct a pixel of the live image, the pixel having a pixel value equal to or less than the first threshold, using a first gain; and
in performing the second brightness correction, correct a pixel of the live image, the pixel having a pixel value equal to or less than the second threshold, using a second gain.

5. An endoscope system comprising:
the endoscopic image processing apparatus according to claim 1; and
an endoscope configured to acquire the live image.

* * * * *